United States Patent [19]

Narukawa

[11] Patent Number: 4,846,292

[45] Date of Patent: Jul. 11, 1989

[54] APPARATUS FOR AUTOMATICALLY MEASURING IGNITION LOSS

[75] Inventor: Akira Narukawa, Yokkaichi, Japan

[73] Assignee: NGK Insulators, Ltd., Japan

[21] Appl. No.: 235,099

[22] Filed: Aug. 23, 1988

[30] Foreign Application Priority Data

Aug. 31, 1987 [JP] Japan .................................. 62-215183

[51] Int. Cl.$^4$ ...................... G01G 19/52; G01G 19/00; G01G 23/00; G01N 25/00

[52] U.S. Cl. ...................................... 177/50; 177/145; 177/245; 364/568; 374/14

[58] Field of Search .......................... 177/50, 145, 245; 364/568; 374/14

[56] References Cited

U.S. PATENT DOCUMENTS

| | | | |
|---|---|---|---|
| 3,717,210 | 2/1973 | Sieswerda | 177/245 X |
| 4,248,315 | 2/1981 | Falinower | 177/145 X |
| 4,391,774 | 7/1983 | Dupain | 177/50 X |
| 4,562,044 | 12/1985 | Bohl | 177/145 X |
| 4,566,804 | 1/1986 | Collins et al. | 177/1 X |
| 4,593,563 | 6/1986 | Laine et al. | 177/50 X |
| 4,623,030 | 11/1986 | Portman, Jr. et al. | 364/568 X |

*Primary Examiner*—George H. Miller, Jr.
*Attorney, Agent, or Firm*—Arnold, White & Durkee

[57] ABSTRACT

An apparatus for automatically and accurately measuring ignition loss of powder samples without requirement of manual handling. The apparatus comprises a weighing section, a heating section and a cooling section which are integrally arranged and the weighing section including a sample supply device and a crucible and tray transporting device. Each of the sections is automatically operated under controlling by a controlling section.

7 Claims, 4 Drawing Sheets

APPARATUS FOR AUTOMATICALLY MEASURING IGNITION LOSS

BACKGROUND OF THE INVENTION

1. Field of the Invention

The present invention relates to an apparatus for accurately and automatically measuring ignition loss of various kinds of powder samples.

2. Related Art Statement

The ignition loss which represents a weight decreased by igniting a powder sample by weight percent is one of the essential chemical characteristics of ceramic materials. The method of measuring the ignition loss is established by a feldspar analyzing method according to JIS M8853 and a pyrophyllite analyzing method according to JIS M8855.

Heretofore, the ignition loss is measured by steps of weighing the weight of a powder sample prior to ignition by means of a balance, manually igniting the sample by using an electric furnace or a Meker burner and subsequently weighing the weight after ignition by means of the balance.

The measuring method of prior art mentioned above has drawbacks such that the efficiency of manually working is decreased and the safety of operators is failed since the ambience becomes a high temperature during the ignition. Furthermore, the measurement values vary widely dependent on operators since the weighing and the heating must be manually handled.

SUMMARY OF THE INVENTION

It is the object of the invention to eliminate the above drawbacks and to provide an apparatus for accurately and automatically measuring the ignition loss without manual handlings.

According to the present invention, for accomplishing the above object, the automatic ignition loss measuring apparatus comprises a weighing section including a weighing device consisting of an electronic balance for measuring a gross weight of a powder sample and a crucible, a sample supply device for selecting a predetermined sample from various kinds of samples to be measured and feeding the selected sample to a crucible on the weighing device and a crucible and tray transporting device for transferring a crucible from a tray to the weighing device, transporting the crucible containing the weighed sample to the tray, transferring the tray retaining the crucible through the following steps of igniting and cooling and finally transporting the crucible from the tray to the weighing device; a heating section including a preheating electric furnace for preheating the crucible containing the weighed sample together with the tray to remove volatile matters at a low temperature, an igniting electric furnace for igniting the preheated crucible retained on the tray to a predetermined high temperature and a crucible tray stacker having a fork for transporting the tray; a cooling section for cooling the heated crucible together with the tray; and a controlled section for controlling operations of the weighing section, heating section and the cooling section.

The word of powder in the specification includes fine powders, coarse powders and granular powders.

According to the present invention, in the arrangement mentioned above, the weighing section adapted for selecting a predetermined sample from various kinds of samples and feeding a predetermined weight of the selected sample to the crucible, the heating section adapted for igniting the samples contained in a plurality of crucibles retained on the tray and the cooling section adapted for cooling the heated crucibles together with the tray are automatically controlled by the controlling section. Accordingly, the ignition loss can be measured in safety manner and in high efficiency.

Furthermore, each of the various kinds of samples is individually contained in the container with the feeder and the sample to be measured is changed by changing the container with the feeder, therefore the feeder is new and clean for every sample so that the samples can be automatically selected and weighed without any contamination with the prior sample.

It is preferable that the container with the feeder is provided with an agitator of blade to permit the powder sample having a tendency of aggregating powder to form lumps of powder in the container to easily pass from the container to the feeder.

Further it is preferable that when the powder sample is weighed by means of the balance simultaneously with feeding of the sample from the container with the feeder to the crucible by vibrating the container by means of the vibrator unit, a voltage applied to the vibrator unit may be stepwisely varied by means of the controller in accordance with the detection of the weight of powder sample supplied to the crucible to change the strength of vibration so as to attenuate the vibration and accurately attain the target weight.

SIMPLE DESCRIPTION OF DRAWING

Some embodiments of the invention will now be described in more detail, by way of example, with reference to the accompanying drawings, in which.

FIGS. 3~6 are a sectional view of embodiments of the container with a feeder.

DESCRIPTION OF THE PREFERRED EMBODIMENTS

Figure 1:
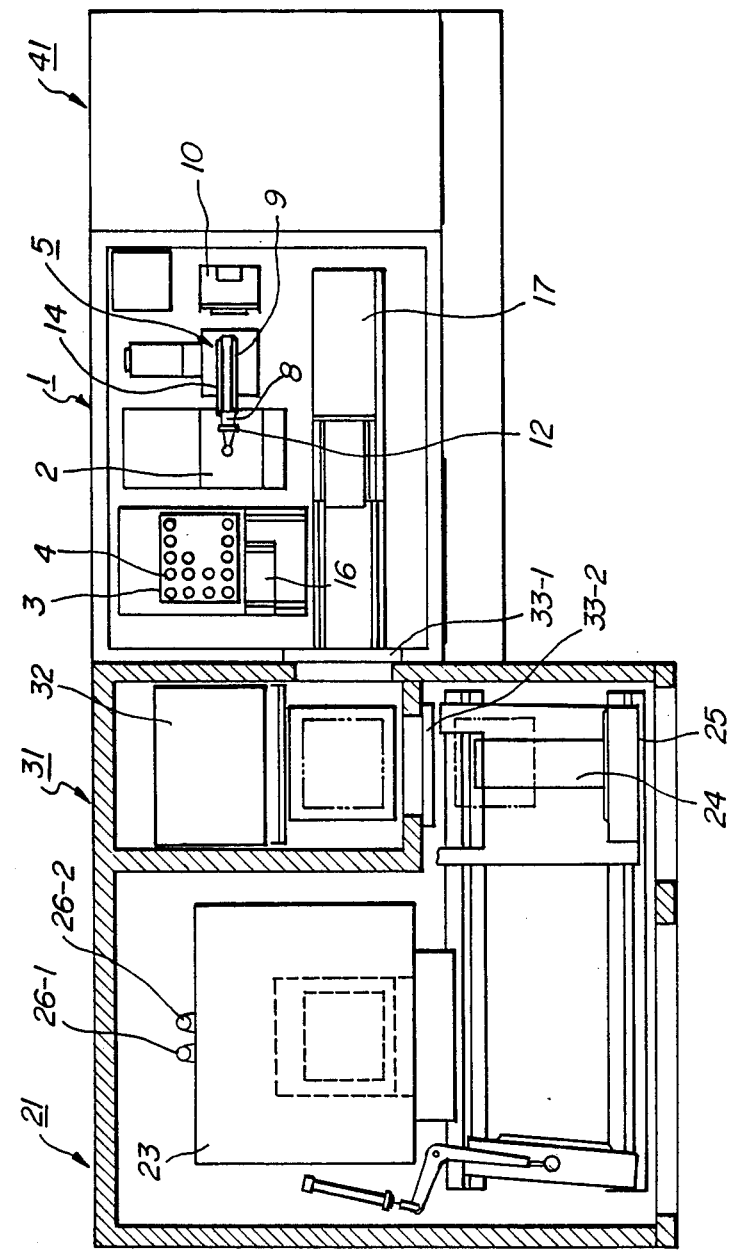
FIG. 1 is a plan view of an embodiment of the measuring apparatus in accordance with the invention.
Figure 2:
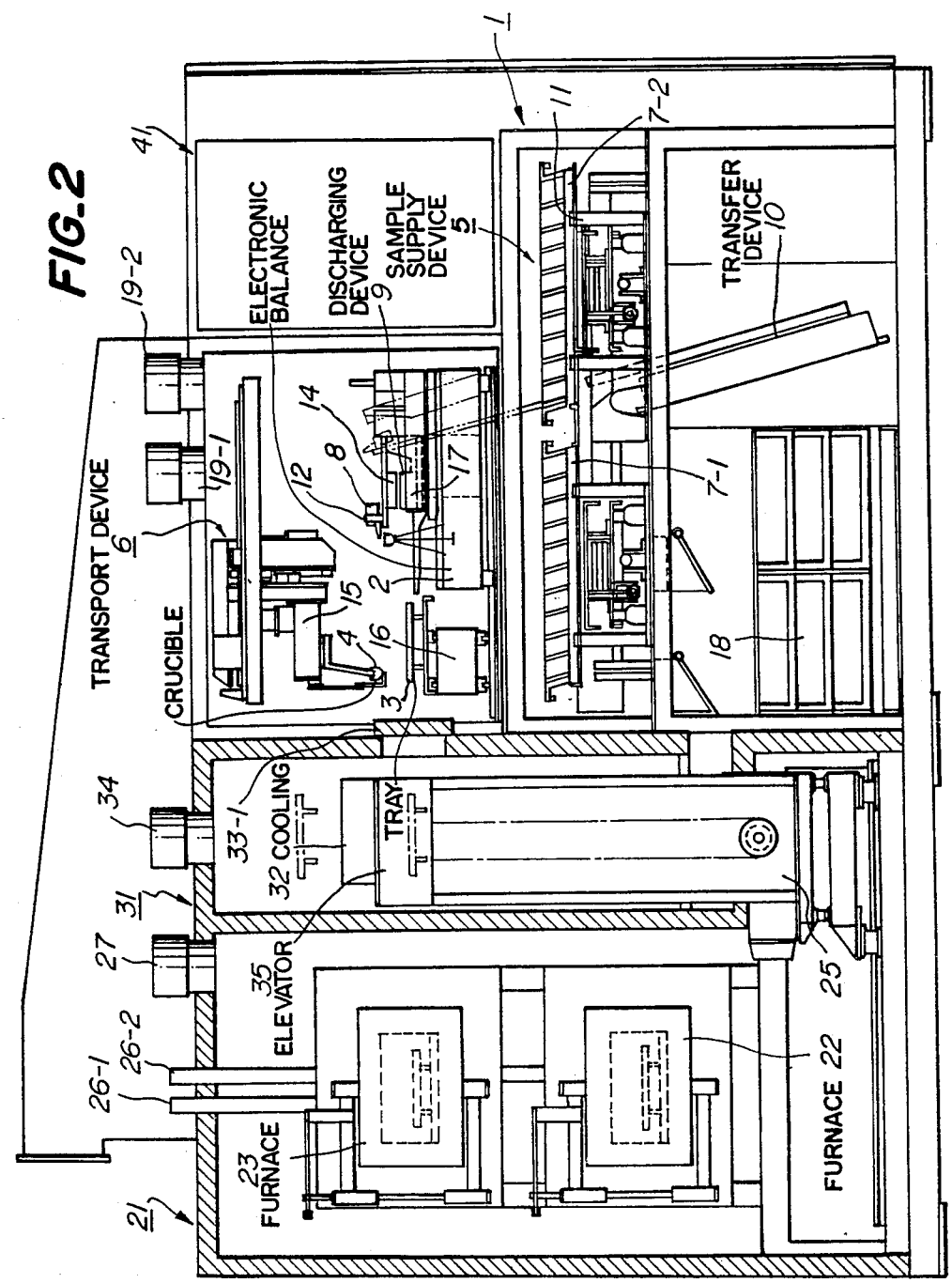
FIG. 2 is an elevational view of the apparatus shown in FIG. 1.
Figure 3:
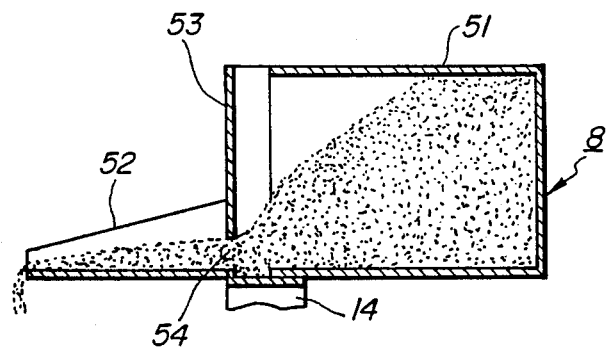

Referring FIGS. 1 and 2 which are an elevational view and a plan view of an embodiment of an apparatus for automatically measuring ignition loss of a sample in accordance with the present invention. The apparatus includes a weighing section 1 comprising an electronic balance 2 for measuring weight of a powder sample fed in a crucible 4 transported from a crucible tray 3, a sample supply device 5 adapted for selecting a sample to be measured from various kind of samples and feeding the selected sample into a crucible 4 mounted on the electronic balance 2 and a device 6 for transporting the crucible tray 3 and is arranged such that the selected sample is weighed in a weighing chamber before and after ignition.

The electronic balance 2 can be selected in accordance with the desired accuracy from conventional electronic balances and in the embodiment, an electronic balance having the maximum weighing value of 200 grams and a reading accuracy of 0.1 milligram may be used. The crucible 4 may be a conventional porcelain crucible or a platinum crucible.

The sample supply device 5 includes a number of sample containers 8 each of which contains a different powder sample to be measured and has a removable cap with a feeder, trays 7-1 and 7-2 for holding the sample containers 8, a sample discharging device 9 having a vibrator unit 14 for discharging the sample in the sample container 8 into a crucible 4 on the electronic balance 2 and a sample container transfer device 10 adapted for selecting a desired container 8 from the sample containers retained in the sample container trays 7-1 and 7-2 and transferring the selected container to the vibrator unit 14 of the sample discharging device 9.

Each of the container trays 7-1 and 7-2 can be transported to the position of the sample container transfer device 10 by means of a sample container tray slide mechanism and further can be transferred to a direction perpendicular to the transport direction from the position of the transfer device 10. After the container 8 containing the next sample to be weighed has reached to the position of the container transfer device 10 by means of the container tray slide mechanism 11, the container is transported to a container clamping mechanism 12 of the sample discharging device 9 inclined as shown by a phantom line in FIG. 2 and is fixed. If a sample container which has been weighed is still clamped to the container clamping mechanism, after the tray slide mechanism 11 is driven to position the sample container trays 7-1 and 7-2 for the used container 8 to be returned at the position of the sample container transfer device 10, the sample container transfer device 10 is driven from the position to return the sample container 8 to the predetermined position and then the sample container 8 is transferred and fixed as mentioned above.

The sample discharging device 9 is returned to a position as shown by a solid line after the sample container 8 to be weighed is fixed by means of the container clamping mechanism 12. The sample in the container 8 is then fed into the crucible 4 on the electronic balance 2 by means of the vibrator unit 14. The vibration caused by the vibrator unit 14 may be constant until the target weight is reached, but alternatively a voltage applied to the vibrator unit is stepwisely varied by means of a controller in accordance with the detection of the weight of powder sample supplied to the crucible 4 to change the strength of vibration so as to attenuate the vibration and accurately attain the target weight.

In the embodiment, the crucible tray transporting device 6 comprises a crucible transfer device 15 adapted for transferring the crucible 4 from the crucible tray 3 to the electronic balance 2 and returning back the crucible 4 containing the weighed sample to the crucible tray 3, a crucible slide table 16 adapted for intermittently transferring the crucible tray and a crucible transferring device 17 adapted for transferring the crucible tray 3 loaded with the crucible 4.

Furthermore, in the embodiment, in order to maintain the atmosphere within all of the weighing section 1 at a dry air condition, the weighing section 1 is provided with a drying device 18 for drying the atmosphere within the weighing device 1 and the drying device is arranged for forcedly drafting air through exhaust ports 19-1 and 19-2. Any conventional moisture absorbents or humidifiers may be used for the drying device 18. It is preferable to feed dry air from the outside into the weighing section.

A heating section 21 comprises a preheating electric furnace 22 adapted for preheating the weighed sample in the crucible 4 retained on the crucible tray 3 to remove volatile matters at a low temperature, an igniting electric furnace 23 for igniting the preheated crucible 4 retained on the crucible tray 3 to a predetermined high temperature and a crucible tray stacker 25 including a fork 24 for transporting the crucible tray 3 loaded with the crucible 4. The preheating electric furnace 22, igniting electric furnace 23 and crucible tray stacker 25 are arranged within a heating chamber. The preheating electric furnace 22 is preferably a muffle furnace which can heat the sample at about 500° C. by means of a Nichrome heater and the igniting electric furnace 23 is preferably a muffle furnace which can ignite the sample at about 1,000° C. by means of a Cantal heater. An electric furnace is, of course, usable for both preheating and igniting. The crucible tray stacker 25 serves for receiving a crucible tray 3 form the preceding step and for delivering it to the following step and for charging and discharging the crucible tray 3 in and out of the preheating electric furnace 22 and the igniting electric furnace 23, respectively. The heating section 21 includes exhaust pipes 26-1 and 26-2 for discharging hot gas from the preheating electric furnace 22 and the igniting electric furnace 23 and an exhaust port 27 for discharging the atmosphere out of the heating chamber.

A cooling section 31 is arranged between the weighing section 1 and the heating section 21 to transfer the crucible tray 3 retaining the crucible 4 with the sample weighed at the weighing section 1 to the heating section 21 for the following heating step and to receive the crucible 4 retained by the crucible tray 3 after ignited and cool it in water or air by means of a cooling device 32. The cooling section 31 is located within a cooling chamber which is airtightly sealed from the weighing section 1 and the heating section 21 by means of openable shutters 33-1 and 33-2, respectively. An elevator 35 for transporting the crucible tray 3 is also arranged in the cooling chamber. The cooling section 31 may be supplied with dry air from the drying device 18 in the weighing section 1 and is provided with an exhaust port 34 for discharging the atmosphere out of the cooling section.

All the operations of the weighing section 1, the heating section 21 and the cooling section 31 are controlled by a control section 41.

FIGS. 3~6 are sectional views of various embodiments of the sample container 8 with a feeder usable in the present invention. The sample container 8 shown in FIG. 3 comprises a container body 51 which may be formed by a conventional glass weighing bottle and a cap 53 which is attached to the container body 51. The cap 53 has a feeder 52 integrally formed with the cap 53. When the sample container 8 is settled on a vibrator unit 14 and is vibrated by the vibrator unit, the sample contained in the container body 21 is fed from the tip of the feeder 52 through an outlet 54 formed in the cap 53 to the crucible 4 set on the electronic balance 2 in response to the vibration by the vibrator unit.

Figure 4:
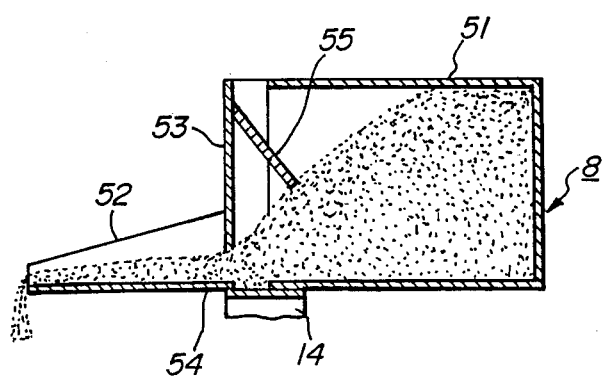

FIG. 4 shows a modification of the sample container 8 with the feeder 52. This container has a blade 55 extending inside the container body 51 for breaking a lump of powder sample grown by the vibration in order to weigh sample more accurately.

Figure 5:
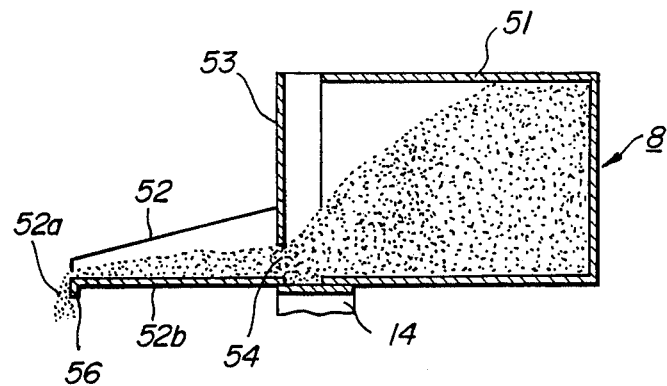

FIG. 5 shows a modification of the sample container 8 having a modified feeder 52 which is preferably used for accurately weighing powder samples which generate a static electricity by vibration. Such a feeder 52 is in the form of a tapered trough having a shape section and is provided with a projection 56 downwardly extended from the front end 52a thereof and thereby the projection 56 prevents the charged powder from adhering on and along the under surface 52b over the front end 52a of the feeder 52. Such an adhered powder finally drops on the balance 5 and affects the weighing of the sample.

Figure 6:
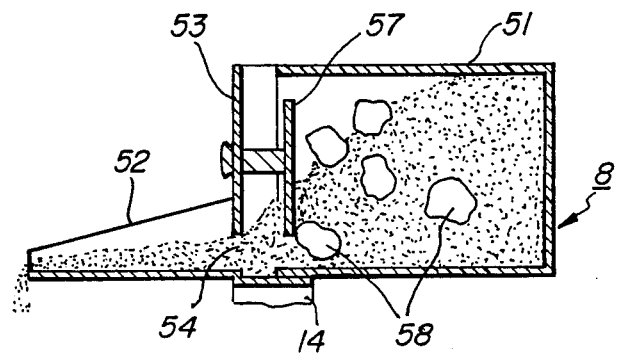

FIG. 6 shows another modification of the sample container 8 which is preferably used for samples having a tendency of aggregating powder to form lumps of powder sample in the container. In this embodiment, a baffle plate 57 in the form of a spider radially extending from the central portion thereof is arranged within the container body 51 to prevent a large particle 58 from feeding out the container 8.

In operation of the above mentioned automatic ignition loss measuring apparatus, firstly, predetermined empty crucibles 4 are set on the crucible tray 3. While, sample containers 8 which are filled with different samples, respectively, are set at the predetermined positions in the sample container trays 7-1 and 7-2 and the position and the kind of the powder are input to the controller 41 together with the weighing sequence. Then, the crucible transporting device 15 of the crucible tray transporting device 6 is driven to transport a crucible 4 from the crucible tray 3 to the electronic balance 2. The predetermined sample container 8 on the sample tray 7-1 or 7-2 is transferred by means of the sample container transfer device 10 and secured to the tip of the tilted sample feeding device 9 by means of the container clamp mechanism 12. After the sample feeding device 9 is returned to the initial position, the vibrator unit 14 begins to vibrate so as to feed a predetermined weight of sample to the crucible 4. Then, the weighed crucible 4 is returned to the given position on the crucible tray 3 by means of the crucible transporting device 15 to complete the weighing step for one sample.

When the crucible tray 3 is filled with the weighed crucibles 4, the crucible tray 3 is transferred to the cooling section 31 from the weighing section 1 through the shutter 33-1 by means of the crucible slide table 16 and the crucible transferring device 17. The crucible tray 3 on the elevator 35 is transferred to the heating section 21 through the shutter 33-2 by means of the crucible tray stacker 25. At the heating section the crucible tray 3 retaining crucibles loaded with the sample is preheated at about 500° C. in the preheating electric furnace 22 and then transferred to the igniting electric furnace 23 by means of the crucible tray stacker 25 and ignited at about 1,000° C. After igniting, the crucible tray 3 is taken out of the igniting electric furnace 23 by means of the crucible tray stacker 25 and transferred to the cooling device 32 in the cooling section 31 through the shutter 33-2. In the cooling device 32 the crucibles on the crucible tray 3 are cooled in water and then in air by means of the cooling device 32. After cooling, the crucible tray 3 is returned to the initial position shown in FIG. 1 by means of the crucible transferring device 17 and the crucible slide table 16 in the weighing section 1. Subsequently, each crucible 4 is again transported by means of the crucible transporting device 15 to the electronic balance 2 for weighing the ignited and cooled sample. Finally, the ignition loss is determined by the initial weight and the weight after igniting at the controlling section 41.

The results of measuring the ignition loss of clay and mixture by use of the automatic ignition loss measuring apparatus according to the present invention are shown in the following Tables 1 and 2 in comparing with prior art, respectively. In the above measuring, platinum crucibles were used.

TABLE 1

|  |  | Invention | Prior art |
|---|---|---|---|
| Ignition loss | 1 | 12.74 | 12.61 |
| (wt %) | 2 | 12.76 | 12.78 |
|  | 3 | 12.69 | 12.86 |
|  | 4 | 12.58 | 12.85 |
|  | 5 | 12.63 | 12.77 |
|  | 6 | 12.70 | 12.71 |
|  | 7 | 12.76 | — |
|  | 8 | 12.73 | — |
| Mean | (wt %) | 12.70 | 12.76 |
| Range | (wt %) | 0.18 | 0.25 |
| Standard deviation | (wt %) | 0.060 | 0.085 |
| Relative standard deviation | (%) | 0.47 | 0.67 |

TABLE 2

| Examples of Measurement of Ignition | | | |
|---|---|---|---|
|  |  | Invention | Prior art |
| Ignition loss | 1 | 4.68 | 4.69 |
| (wt %) | 2 | 4.69 | 4.63 |
|  | 3 | 4.72 | 4.62 |
|  | 4 | 4.70 | 4.65 |
|  | 5 | 4.63 | 4.63 |
|  | 6 | 4.67 | 4.71 |
|  | 7 | 4.70 | 4.62 |
|  | 8 | 4.71 | 4.64 |
| Mean | (wt %) | 4.69 | 4.65 |
| Range | (wt %) | 0.09 | 0.09 |
| Standard deviation | (wt %) | 0.028 | 0.033 |
| Relative standard deviation | (%) | 0.60 | 0.71 |

It is understood from the results shown in the Tables 1 and 2, the ignition loss can be automatically weighed more accurately in use of the automatic ignition loss measuring apparatus according to the invention than in the prior art.

Obviously, the invention is not limited to the embodiments described above and is possible to variously modify or change within the scope of the invention. For example, number of sample containers and trays is not limited to the embodiment described above.

It is understood from the above that in the automatic ignition loss measuring apparatus according to the present invention, the weighing section, the heating section and the cooling section are integrally arranged and controlled by the controlling section, therefore it is possible to measure automatically the ignition loss without manual operation in safety manner and in high efficiency. Furthermore it can be constantly accomplished a high measurement accuracy and faculty of the measuring apparatus independent of the technical skill of operators.

What is claimed is:

1. An apparatus for automatically measuring ignition loss comprising a weighing section including a weighing device consisting of an electronic balance for measuring weight of a powder sample, a sample supply device for selecting a predetermined sample from various kinds of samples to be measured and feeding the selected sample to a crucible on the weighing device and a crucible and tray transporting device for transferring a crucible from a tray to the weighing device, transporting the crucible containing the weighed sample to the tray, transferring the tray retaining the crucibles for igniting and cooling and finally transporting the crucible from the tray to the weighing device;

a heating section including a preheating electric furnace for preheating the crucible containing the weighed sample together with the tray to remove volatile matters at a low temperature, an igniting electric furnace for igniting the preheated crucible retained on the tray to a predetermined high temperature and a crucible tray stacker having a fork for transporting the tray;

a cooling section for cooling the heated crucible together with the tray; and a control section for controlling operations of the weighing section, the heating section and the cooling section.

2. An apparatus as claimed in claim 1, wherein said sample supply device comprising a sample container for containing powder sample to be measured, the container being retained on a sample container tray and including a detachable cap having a feeder integrally formed with the cap; a sample discharging device including a vibrator unit for feeding the sample from the sample container to the crucible on the weighing device; and a sample container transporting device for selecting a predetermined sample container from sample containers retained on the sample container tray and transporting the selected sample container to the vibrator unit of the sample discharging device.

3. An apparatus claimed in claim 2, wherein said sample container has a blade extending from the inner wall of the container for preventing the powder sample from forming a lump of powder in the interior of the container.

4. An apparatus as claimed in claim 2, wherein said feeder has a projection downwardly extended from the front end of the feeder.

5. An apparatus as claimed in claim 2, wherein said sample container has a baffle plate arranged within the container for prevent a large particle of sample from feeding out of the container.

6. An apparatus claimed in claim 2, wherein said sample supply device is arranged for continuously detecting the weight of sample supplied to the crucible from the sample container through the feeder and for controlling the vibration of the sample container with the feeder by the vibrator unit to ensure the target weight.

7. An apparatus claimed in claim 1, wherein said crucible and tray transporting device is consisted of a crucible transporting device adapted for transporting a crucible from the tray to the weighing device and a crucible containing the weighed sample to the tray, a crucible tray slide table adapted for intermittently transferring the crucible tray and a crucible transferring device adapted for transferring the crucible between the cooling section and the crucible tray slide table together with the crucible tray.

* * * * *